US011304974B2

(12) United States Patent
Lostao Camón

(10) Patent No.: US 11,304,974 B2
(45) Date of Patent: Apr. 19, 2022

(54) NANOSYSTEMS COMPRISING SILVER AND ANTIBIOTICS AND THEIR USE FOR THE TREATMENT OF BACTERIAL INFECTIONS

(71) Applicant: Luis Jesús Lostao Camón, Saragossa (ES)

(72) Inventor: Luis Jesús Lostao Camón, Saragossa (ES)

(73) Assignee: LABORATORIOS ENOSAN, S.L., Saragossa (ES)

( * ) Notice: Subject to any disclaimer, the term of this patent is extended or adjusted under 35 U.S.C. 154(b) by 0 days.

(21) Appl. No.: 16/489,207

(22) PCT Filed: Apr. 9, 2018

(86) PCT No.: PCT/EP2018/059006
§ 371 (c)(1),
(2) Date: Aug. 27, 2019

(87) PCT Pub. No.: WO2018/189095
PCT Pub. Date: Oct. 18, 2018

(65) Prior Publication Data
US 2020/0330509 A1   Oct. 22, 2020

(30) Foreign Application Priority Data

Apr. 10, 2017   (EP) .................................... 17382196

(51) Int. Cl.
*A61K 33/38* (2006.01)
*A61K 9/00* (2006.01)
(Continued)

(52) U.S. Cl.
CPC ............ *A61K 33/38* (2013.01); *A61K 9/0053* (2013.01); *A61K 9/08* (2013.01); *A61K 9/14* (2013.01); *A61K 38/14* (2013.01); *A61K 47/02* (2013.01)

(58) Field of Classification Search
CPC ........ A61K 33/38; A61K 9/0053; A61K 9/14; A61K 38/14; A61K 47/02; A61K 38/12;
(Continued)

(56) References Cited

U.S. PATENT DOCUMENTS

| 2003/0108612 A1 | 6/2003 | Xu et al. |
| 2009/0148484 A1 | 6/2009 | Lin et al. |
| 2015/0174079 A1* | 6/2015 | Davis ..................... A61K 33/38 424/618 |

FOREIGN PATENT DOCUMENTS

| ES | 135695 U | 5/1968 |
| FR | 784959 A | 7/1935 |

(Continued)

OTHER PUBLICATIONS

Hari et al, Comparative Study on the Synergistic Action of Differentially Synthesized Silver Nanoparticles with Beta-Cephem Antibiotics and Chloramphenicol, Journal of Nanoscience, Article ID 201482 (Year: 2014).*

(Continued)

*Primary Examiner* — Carlos A Azpuru
(74) *Attorney, Agent, or Firm* — Cantor Colburn LLP

(57) ABSTRACT

A composition including metallic silver nanoparticles is supported on a carrier, wherein the carrier is in the form of particles. The carrier is selected from an inert carrier or an antibiotic. The composition further includes at least one antibiotic in the case the carrier is an inert carrier. A related nanosystem includes a composition having metallic silver nanoparticles or a mixture of silver nanoparticles and at least one antibiotic for use in the treatment of an infection caused by at least one strain of bacteria resistant to at least one antibiotic. Pharmaceutical compositions and methods for the preparation of these compositions and nanosystems are also used for the treatment of bacterial infections.

18 Claims, 2 Drawing Sheets

(51) Int. Cl.
  *A61K 9/08* (2006.01)
  *A61K 9/14* (2006.01)
  *A61K 38/14* (2006.01)
  *A61K 47/02* (2006.01)

(58) Field of Classification Search
  CPC ............... A61K 31/165; A61K 31/351; A61K 31/4178; A61K 31/43; A61K 31/5377; A61K 31/545; A61K 31/575; A61K 31/65; A61K 31/665; A61K 31/7056; A61K 9/501; A61K 9/1611; A61K 9/1676; A61K 31/1496; Y02A 9/501
  See application file for complete search history.

(56) References Cited

FOREIGN PATENT DOCUMENTS

| JP | 6166623 A | 6/1994 |
|---|---|---|
| JP | 10120518 A | 5/1998 |
| JP | 201163525 A | 3/2011 |
| WO | 2006074117 A2 | 7/2006 |
| WO | 2013063405 A1 | 5/2013 |
| WO | 2018/189095 A1 * | 10/2018 |

OTHER PUBLICATIONS

International Search Report dated May 24, 2018 re: Application No. PCT/EP2018/059006, pp. 1-4.
Written Opinion dated May 24, 2018 re: Application No. PCT/EP2018/059006, pp. 1-5.
Madalina Tudose et al. "Antibacterial Activity Evaluation of Silver Nanoparticles Entrapped in Silica Matrix Functionalized with Antibiotics", J. Inorg Organomet Polym, 2015, pp. 1-11.
Natarajan Krishnan et al. "Silver Nanoparticles Functionalized Tyrocidine Hydrochloride: A New Antimicrobial Complex for the Management of Skin Wound Infections", Application No. 1963/CHE/2015, Apr. 16, 2015, pp. 1-26.
JP Office Action dated Jan. 28, 2022 re: Application No. 2019-541069, pp. 1-8, citing: I.J. Inorg. Organomet, Appln No. 2015CHE1963, JP H 6-166623A, JP H 10-120518A and JP 2011-63525A.

* cited by examiner

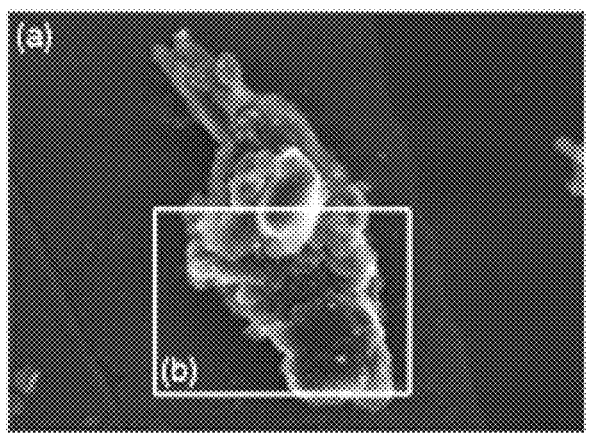
Figure 1(a)
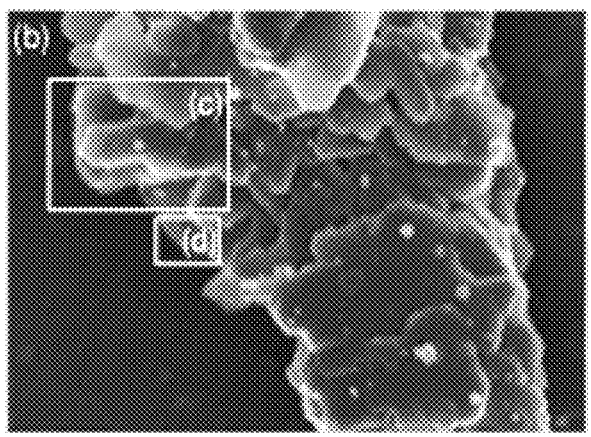
Figure 1(b)
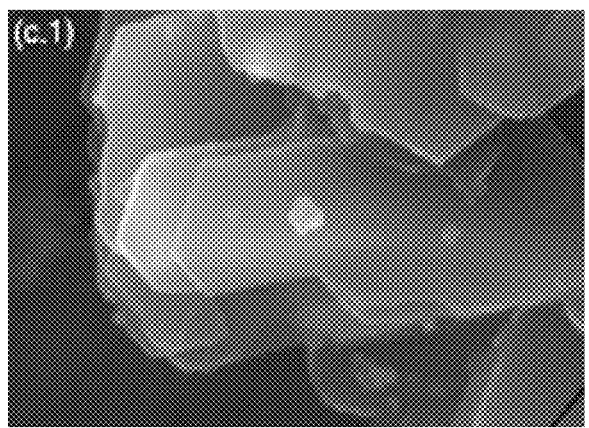
Figure 1(c.1)

Figure 1(c.2)

NANOSYSTEMS COMPRISING SILVER AND ANTIBIOTICS AND THEIR USE FOR THE TREATMENT OF BACTERIAL INFECTIONS

TECHNICAL FIELD

The present disclosure is related to uses of silver nanoparticles, in combination with antibiotics, for the treatment of infections caused by resistant bacteria, as well as to compositions comprising supported silver nanoparticles and antibiotics.

BACKGROUND

Antibiotics and Antibiotic Resistance

Antibiotics are medicines used to prevent and treat bacterial infections. They may either kill (bactericidal) or inhibit the growth of bacteria (bacteriostatic) and are classified based on their mechanism of action, chemical structure or spectrum of activity.

Antibiotic resistance occurs when bacteria change in response to the use of these medicines. Bacteria, not humans or animals, become antibiotic-resistant. These bacteria may infect humans and animals, and the infections they cause are harder to treat than those caused by non-resistant bacteria. It leads to a reduction in the effectiveness of a drug such as an antibiotic in curing a disease or condition. Some bacteria are naturally resistant to certain antibiotics while others can acquire resistance through mutations in some of their genes when they are exposed to an antibiotic. This resistance—natural or acquired—can spread to other bacterial species since bacteria can easily exchange genetic material from one to another, even if they are from different species.

Antibiotic resistance is rising to dangerously high levels in all parts of the world. New resistance mechanisms are emerging and spreading globally, threatening our ability to treat common infectious diseases. A growing list of infections—such as pneumonia, tuberculosis, blood poisoning and gonorrhoea—are becoming harder, and sometimes impossible, to treat as antibiotics currently used become less effective.

Where antibiotics can be bought for human or animal use without a prescription, the emergence and spread of resistance is made worse. Similarly, in countries without standard treatment guidelines, antibiotics are often over-prescribed by health workers and veterinarians and over-used by the public.

We may be heading for a post-antibiotic era, in which common infections and minor injuries can once again kill. Antibiotic resistance leads to higher medical costs, prolonged hospital stays, and increased mortality.

On the one hand, there is a need to change the way antibiotics are prescribed and used.

On the other hand, new treatments, able to treat infections caused by antibiotic resistant bacteria, need to be developed.

Antimicrobial Use of Silver

Prior to the introduction of modern antibiotics, colloidal silver was used as a germicide and disinfectant: e.g. in 1920, Searle, A. B. disclosed in "*Chapter VIII: Germicides and Disinfectants*". *The Use of Colloids in Health and Disease. Gerstein—University of Toronto:Toronto Collection: London Constable & Co.*" that silver collosol solution was mixed with nutrient broth in various dilutions, inoculated with typhoid bacillus and incubated, showing germicidal power. Other experiments of similar nature are mentioned in the same publication, demonstrating the value of silver collosols as bactericides having a strong germicidal action, in contrast to other metal colloids having no or only slight germicidal action. Also, the use of silver supported over inert carriers was used for these bactericide purposes (Spanish patent 135,695 o FR 784 959).

With the development of modern antibiotics in the 1940s, the use of silver as an antimicrobial agent diminished.

More recently, in view of antibiotic resistance in many bacterial strains, the use of colloidal silver is being explored again, especially applying the developments in the nanotechnology field, the nanosize being able to change chemical, physical and optical properties of metals. The use of silver nanoparticles and colloidal silver as an antimicrobial agent by itself for treating bacterial infections is explored in several publications (see e.g. Rai, M et al. "*Silver Nanoparticles as A New Generation of Antimicrobials*" *Biotechnol. Adv.* 2009, 27, 76-83; Rizzello, L. et al. "*Nanosilver-Based Antibacterial Drugs and Devices: Mechanisms, Methodological Drawbacks, and Guidelines.*" *Chem. Soc. Rev.* 2014, 43, 1501-1518; and US2009148484).

Combinations of Silver and Antibiotics

Silver has not only been tried to be used alone as an antimicrobial agent, but has also been used in combination with antibiotics.

For example, in 1968 a compound containing silver and the antibiotic sodium sulfadiazine, silver sulfadiazine (SSD), was developed (see e.g. Chopra I (2007). "*The increasing use of silver-based products as antimicrobial agents: a useful development or a cause for concern?*". *J. Antimicrob. Chemother.* 59 (4): 587-90). Nevertheless, its use has been limited to topical applications, and other antibiotics were found to be more effective, and thus its use is hardly recommended. In fact, its effectiveness was questioned in the review "*Cochrane Database Syst Rev.* 2010 Mar. 17; (3):CD006478", wherein it was stated that "there is insufficient evidence to establish whether silver-containing dressings or topical agents promote wound healing or prevent wound infection".

The use of silver in a new class of inorganic antimicrobial agents has emerged, namely silver nanocluster constructs, packed with daptomycin. Each nanocluster construct, being in the ultrasmall particles range, contains 16 silver atoms and 9 glutathione protecting ligands. These nanoclusters are homogeneously conjugated with daptomycin being in the same size range, through a strong covalent bond (see Zheng et al. "*Antimicrobial Cluster Bombs: Silver Nanoclusters Packed with Daptomycin*", *ACS Nano* (2016), 10 (8), 7934-7942). It is stated that bulkier silver nanoparticles instead of the silver nanoclusters, in conjunction with daptomycin, would reduce the antimicrobial efficiency of the hybrid.

Physical mixtures of colloidal silver with several antibiotics have also been explored. Nanoparticles of silver, both elemental silver and elemental silver coated by silver oxides, have been mixed with several antibiotics and tested for activity. Some additive antimicrobial activity was found (see WO2006074117).

More recently, the action of silver ions in combination with antibiotics has been tested both in vitro and in vivo. It was found that silver, in the form of dissolved ions, attacks bacterial cells in two main ways: it makes the cell membrane more permeable, and it interferes with the cell's metabolism, leading to the overproduction of reactive, and often toxic, oxygen compounds. (see "*Science Translational Medicine*

19 Jun. 2013: Vol. 5, Issue 190, pp. 190ra81" and WO 2013/063405 A1, by the same author). Further research combining silver ions and antibiotics is suggested in these documents. Nevertheless, no results are disclosed for metallic silver. Given the differences in behavior and physico-chemical properties between ionic silver and metallic silver, and specifically nanoparticles, these documents cannot shed light on the usefulness as antibiotics of metallic silver. On the other hand, ionic silver has the drawback that it has been described to exhibit toxic effects when administered to mammals, including human beings, and may cause blue coloration due to reduction processes occurring in the living body.

Resistance to antibiotics and therefore the search for new antibiotics in the fields of medicine is a pressing need which has even been the object of a specific report drafted and published by the World Health Organization in 2014. It is a problem that has even been discussed within the UN in September 2016.

BRIEF DESCRIPTION OF THE DRAWINGS

FIG. 1(a) shows Kaolin microparticles with deposited silver nanoparticles thereon (x8870);

FIG. 1(b) shows at x20380 the area highlighted in FIG. 1(a);

FIG. 1(c.1) shows at x66000 the area (c) highlighted in FIG. 1(b). Silver nanoparticles can be clearly appreciated on the surface of the laminar structure of Kaolin;

FIG. 1(c.2) shows the Silver nanoparticles (white color) when observed under backscattered electrons, as opposed to areas having no Silver nanoparticles.

SUMMARY

Figure 1D:
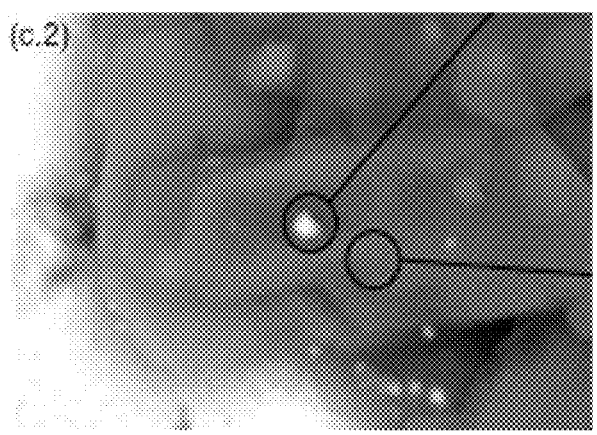
FIG. 1(d) shows at x66000 the area (d) highlighted in FIG. 1(b). Silver nanoparticles can be clearly appreciated on the edges of the laminar structure of Kaolin.

There is thus a need to provide new antimicrobial treatments, due to the rising of bacterial resistance to antibiotics. The present disclosure provides new compositions and treatments of bacterial infections, namely it is related to uses of metallic silver nanoparticles in combination with antibiotics, for the treatment of infections caused by resistant bacteria, as well as to compositions comprising metallic silver nanoparticles and antibiotics.

A first aspect of the present disclosure refers to a composition that comprises metallic silver nanoparticles which are supported on a carrier, the carrier being in the form of particles; said carrier is selected either from an inert carrier or an antibiotic; in case the carrier is an inert carrier, the composition further comprises at least one antibiotic.

A second aspect of the present disclosure refers to the use of a nanosystem that comprises either a composition according to the first aspect defined above or a mixture of silver nanoparticles and at least one antibiotic, for use in the treatment of an infection caused by at least one strain of bacteria resistant to at least one antibiotic.

Further, the present disclosure relates to a preparation process of the composition according to the first aspect of the disclosure as defined above.

The present disclosure is also related to a pharmaceutical composition which comprises at least one pharmaceutically acceptable excipient and a composition that comprises metallic silver nanoparticles supported on a carrier, according to the first aspect of the disclosure, for use as a medicament; for use in the treatment of an infection; and for oral use in the treatment of an infection.

DETAILED DESCRIPTION OF THE DRAWINGS

A first aspect of the present disclosure refers to a composition that comprises silver nanoparticles which are supported on a carrier, which is in the form of particles; said carrier is selected either from an inert carrier or an antibiotic; in case the carrier is an inert carrier, the composition further comprises at least one antibiotic.

The inert carrier is preferably selected from, but is not limited to, a clay, zeolites, silica, alumina, kaolin, and metal oxides (e.g. MgO). According to a preferred embodiment, the inert carrier is kaolin, a rock rich in kaolinite, which is a clay mineral with the chemical composition $Al2Si_2O_5(OH)_4$.

In the frame of the present disclosure, "supported" means any one of adsorbed on the surface, impregnated on the surface, embedded on the surface, etc. of the pulverized carrier. i.e., silver nanoparticles are adhered to the surface of the pulverized carrier, as a consequence of surface energies. The atoms on the surface of the carrier (either an inert carrier or an antibiotic, in the frame of the present disclosure) may attract and bond to other atoms, in this case silver atoms, the nature of the bonding being weak van der Waals forces, covalent bondings, or electrostatic attraction. Therefore, the compositions of the disclosure are simple to prepare and the carrier, whether inert or an antibiotic, does not need additional ligands in order to effectively associate with the metallic silver nanoparticles.

In the frame of the present disclosure "inert carrier" refers to a carrier on which the metallic silver nanoparticles are supported, which does not have a pharmaceutical activity, and specifically does not have any antibiotic activity.

The carrier is preferably pulverized to microparticles, a size which allows efficient interaction with the metallic silver nanoparticles, while allowing its pharmaceutical applications. The typical mean particle diameter for the inert carrier is 0.1 μm (micrometer) or above, preferably 0.25 μm or above, and more preferably 0.5 μm or above. The typical mean particle diameter for the inert carrier are 200 μm or below, preferably 100 μm or below, more preferably 50 μm or below. Most preferably the mean particle diameter is between 0.5 and 50 μm.

The typical mean particle diameter for the antibiotic when used as a carrier is 0.1 μm (micrometer) or above. The Typical mean particle diameter for the antibiotic carrier are 200 μm or below, preferably 100 μm or below, more preferably 50 μm or below. Most preferably the mean particle diameter is between 0.1 and 50 μm.

The metallic silver nanoparticles in the compositions of the present disclosure typically have a diameter between 1 and 100 nanometers. Preferably, the diameter is above about 5 nanometers, more preferably above about 10 nanometers, even more preferably above about 15 nanometers, and mostly preferably above about 20 nanometers. Most preferably, the diameter is between about 20 nanometers and about 50 nanometers.

The antibiotic of the composition according to any one of the aspects of the present disclosure (e.g. first aspect or second aspect), whether used as component (e.g. mixed with the metallic silver nanoparticle supported on an inert carrier) or whether it is itself acting as the pulverized carrier of the metallic silver nanoparticle, is preferably selected from, but is not limited to, penicillins (including aminopenicillins, antipseudomonal penicillins, beta-lactamase inhibitors, natural penicillins, and penicillinase resistant penicillins), cephalosporins, monobactams, beta lactamase inhibitors, carbapenems, aminoglucosides, quinolones, tetracyclines, glycopeptides, lincomycins, macrolides, ketolides, sulfonamides, aminoglycosides, oxazolidinones or from the group comprising colistin, sulfamethoxazole/trimethoprim, fosfomycin, nitrofurantoin, chloramphenicol, clindamycin, fusidic acid, linezolid, mupirocin, daptomycin, clindamycin and rifampicin.

Aminopenicillins include, but are not limited to, amoxicillin (e.g. Amitron®, Clamoxyl®, Amoxicot®, Moxatag®, Moxilin®, Amoxil®, Apo-Amoxi®, DisperMox®, Trimox®) and ampicillin (Principen®, Omnipen-N®, Britapen®, Gobemicina®, Retarpen®, Amplipeni®, Pembrintin®)

Antipseudomonal penicillins include, but are not limited to, carbenicillin (e.g. Geocillin®, Carbapen®, Fugacillin®, Geopen®, Pyocianil®), piperacillin (e.g. Pipracil®) and ticarcillin (e.g. Ticar®).

Beta-lactamase inhibitors include, but are not limited to, combinations of amoxicillin/clavulanate (e.g. Augmentin®, Augmentine®, Clavulin®, Amoclan®, Curam®, Optamox®, Moxtam®, Cla-Biomox®), ampicillin/sulbactam (e.g. Unasyn®), piperacillin/tazobactam (e.g. Zosyn®) and clavulanate/ticarcillin (e.g. Timentin®).

Natural penicillins include, but are not limited to, penicillin V potassium (e.g. Beepen-VK, PC Pen VK, Veetids), penicillin g benzathine (e.g. Bicillin L-A®, Isoject Permapen®), penicillin g potassium (e.g. Prizerpen®), procaine penicillin (e.g. Wycillin®) and a combination of penicillin g benzathine/procaine penicillin (e.g. Bicillin C-R®).

Penicillinase resistant penicillins include, but are not limited to, oxacillin (e.g. Bactocill®), dicloxacillin (e.g. Dycill®, Dynapen®) and nafcillin (e.g. Unipen®).

Tetracyclines include, but are not limited to, doxycycline (e.g. Acticlate®, Adoxa®, Adoxa CK®, Adoxa Pak®, Adoxa TT®, Alodox®, Avidoxy®, Doryx®, Doxy 100®, Doxy 200®, Mondoxyne NL®, Morgidox®, Ocudox®, Oracea®, Oraxyl®, Periostat®, Targadox®, Uracil®, Vibra-Tabs®, Vibramycin®), tetracycline (e.g. Sumycin®, Actisite®, Ala-Tet®) and minocycline (e.g. Cleeravue-M®, Dynacin®, Minocin®, Myrac®, Solodyn®, Ximino®).

There are five generations of cephalosporins; they are generally classified into cephalosporins/beta-lactamase inhibitors, first generation cephalosporins, fourth generation cephalosporins, next generation cephalosporins, second generation cephalosporins, and third generation cephalosporins.

Cephalosporins/beta-lactamase inhibitors include, but are not limited to, avibactam/ceftazidime (e.g. Avycaz®) and ceftolozane/tazobactam (e.g. Zerbaxa®).

First generation cephalosporins include, but are not limited to, cefadroxil (e.g. Duricef®), cephradine (e.g. Velosef®), cefaclor (e.g. Raniclor®), cefdinir (e.g. Omnicef®), cefazolin (e.g. Ancef®), cefditoren (e.g. Spectracef®), cefpodoxime (e.g. Vantin®), cefprozil (e.g. Cefzil®), ceftibuten (e.g. Cedax®), cefuroxime e.g. (Ceftin®), and cephalexin (e.g. Keflex®, Biocef®, Panixine®).

Fourth generation cephalosporins include, but are not limited to, cefepime (e.g. Maxipime®).

Next generation cephalosporins include, but are not limited to, ceftaroline (e.g. Teflaro®).

Second generation cephalosporins include, but are not limited to, loracarbef (e.g. Lorabid®), cefotetan (e.g. Cefotan), cefuroxime (Zinacef®, Ceftin®), cefprozil (e.g. Cefzil®), cefoxitin (e.g. Mefoxin®), and cefaclor (e.g. Raniclor®).

Third generation cephalosporins include, but are not limited to, ceftibuten (e.g. Cedax®), ceftriaxone (e.g. Rocephin®), cefotaxime (e.g. Claforan®), cefpodoxime (e.g. Vantin®), cefdinir (e.g. Omnicef®), cefixime (e.g. Suprax®), cefditoren (e.g. Spectracef®), ceftizoxime (e.g. Cefizox), cefoperazone (e.g. Cefobid®), and ceftazidime (e.g. Ceptaz®, Fortaz®, Tazicef®).

Quinolones include, but are not limited to, lomefloxacin (e.g. Maxaquin®), ofloxacin (e.g. Floxin®), norfloxacin (e.g. Noroxin®), gatifloxacin (e.g. Tequin), ciprofloxacin (e.g. Cipro®, Proquin®), moxifloxacin (e.g. Avelox®), levofloxacin (e.g. Levaquin®), gemifloxacin (e.g. Factive®), cinoxacin (e.g. Cinobac®), nalidixic acid (e.g. NegGram®), trovafloxacin (e.g. Trovan®), and sparfloxacin (e.g. Zagam®), Lincomycins include, but are not limited to, lincomycin (e.g. Lincocin®), and clindamycin (e.g. Cleocin®).

Ketolides include, but are not limited to, telithromycin (e.g. Ketek®).

Macrolides include, but are not limited to, erythromycin (e.g. Erythrocin®, Ery-Tab®, Eryc®, Ilosone®), azithromycin (e.g. Zmax®, Zithromax®, Zitromax®, clarithromycin (e.g. Biaxin®), and fidaxomicin (e.g. Dificid®).

Sulfonamides include, but are not limited to, sulfizoxazone (e.g. Gantrisin®, Truxazole®), sulfasalazine (e.g. Azulfidine) and a combination of sulfamethoxazole/trimethoprim (e.g. Sulfatrim, Co-trimoxazole®, Septra®, Bactrim®, Cotrim®).

Glycopeptide Antibiotics include, but are not limited to, vancomycin (e.g. Vancocin®), dalbavancin (e.g. Dalvance®), oritavancin (e.g. Orbactiv®), and telavancin (e.g. Vibativ®)

Aminoglycosides include, but are not limited to, paromomycin (e.g Paromycin®, Humatin®), tobramycin (e.g. Tobi®, Bethkis®, Kitabis®, Nebcin®, TOBI Podhaler®), gentamicin (e.g. Garamycin®), amikacin (e.g. Amikin®), kanamycin (e.g. Kantrex®) and neomycin (Neo-Fradin®, Neo-Tab®).

Carbapenems include, but are not limited to, doripenem (e.g. Doribax®), meropenem (e.g. Merrem®), ertapenem (e.g. Inanz®) and a combination of imipenem/cilastatin (e.g. Primaxin®).

For example the antibiotic is selected from Penicillins, Cephalosporins, Monobactams, β-lactamase inhibitors, Carbapenems, Aminoglycosides, Quinolones, Tetracyclines, Glycopeptides or from the group comprising colistin, sulfamethoxazole/trimethoprim, fosfomycin, nitrofurantoin, chloramphenicol, clindamycin, fusidic acid, linezolid, mupirocin, daptomycin, clindamycin and rifampicin.

In the case the antibiotic is a Penicillin, it is preferably selected from Ampicillin, Piperacillin, Mezlocillin, Oxacillin, Penicillin, Penicillin G. Even more preferably, it is Penicillin G.

In the case the antibiotic is a Cephalosporin, it is preferably selected from Cefazolin, Cefuroxime, Cefpodoxime, Cefotaxime, Ceftazidime, Cefoxitin and Cefepime.

In the case the antibiotic is a Monobactams, it is preferably Aztreonam.

In the case the antibiotic is a β-lactamase inhibitor, it is preferably selected from Amoxicilline/Clavulanic Acid, Ampicilline/Sulbactam, Piperacillin/tazobactam, Cefotaxime/Clavulanic Acid and Ceftazidime/Clavulanic Acid.

In the case the antibiotic is a Carbapenems, it is preferably selected from Ertapenem, Meropenem and Imipenem.

In the case the antibiotic is an Aminoglycoside, it is preferably selected from Amikacin, Gentamicin and Tobramycin.

In the case the antibiotic is a Quinolone, it is preferably selected from Levofloxacin, Ciprofloxacin, Moxifloxacin and Norfloxacin.

In the case the antibiotic is a Tetracycline, it is preferably selected from Tetracycline, Tigecycline, Azithromycin and Erythromycin.

In the case the antibiotic is a Glycopeptide, it is preferably selected from Vancomycin and Teicoplanin. Preferably, the antibiotic is Vancomycin.

Other preferred antibiotics are Colistin, Trimethoprim/Sulfamethoxazole, Fosfomycin, Nitrofurantoin, Chloramphenicol, Linezolid, Mupirocin, Daptomycin, Clindamycin, Rifampicin and Fusidic acid. Preferably, the antibiotic is selected from Linezolid and Daptomycin. Even more preferably, the antibiotic is Linezolid.

Thus, most preferably, the antibiotic is selected from Ampicillin, Piperacillin, Mezlocillin, Oxacillin, Penicillin, Penicillin G, Cefazolin, Cefuroxime, Cefpodoxime, Cefotaxime, Ceftazidime, Cefoxitin, Cefepime, Aztreonam, Amoxicilline/Clavulanic Acid, Ampicilline/Sulbactam, Piperacillin/tazobactam, Cefotaxime/Clavulanic Acid and Ceftazidime/Clavulanic Acid, Ertapenem, Meropenem, Imipenem, Amikacin, Gentamicin, Tobramycin, Levofloxacin, Ciprofloxacin, Moxifloxacin, Norfloxacin, Tetracycline, Tigecycline, Azithromycin, Erythromycin, Vancomycin, Teicoplanin, Colistin, Trimethoprim/Sulfamethoxazole, Fosfomycin, Nitrofurantoin, Chloramphenicol, Linezolid, Mupirocin, Daptomycin, Clindamycin, Rifampicin and Fusidic acid.

In the case the carrier in the composition according to the first aspect of the present disclosure is an inert carrier, any one of the above listed particular inert carriers (i.e. a clay, zeolites, silica, alumina, kaolin, and metal oxides (e.g. MgO)) may be combined with any one of the listed particular antibiotics. Even more, the composition may comprise one or more particular antibiotics selected from the antibiotics listed above, in combination with any one of the inert carriers.

Within the composition, the weight ratio of metallic silver with respect to the total amount of antibiotics is between 10:100 and 0.1:100.

The composition may further contain any kind of at least one pharmaceutically acceptable excipient known in the Art; it will be evident to one skilled in the Art to select the excipient according to the chosen route of administration. The excipient may be one or more selected from one or more of antiadherents, binders, coatings, colourings, disintegrants, flavors, glidants, lubricants, preservatives, sorbents, sweeteners o vehicles, as known in the Art.

The route of administration may be any known route of administration, for example a route of administration selected from, but not limited to, oral, topical, sublingual, parenteral, rectal administration, by inhalation, or by intravenous, intramuscular, subcutaneous injection.

A second aspect of the present disclosure refers to a nanosystem that comprises either a composition according to the first aspect of the disclosure as defined above, or a mixture of silver nanoparticles and at least one antibiotic, for use in the treatment of an infection caused by at least one strain of bacteria resistant to at least one antibiotic. In this context, the silver nanoparticles may be selected from either silver nanoparticles being in a suspension, or colloidal silver.

Colloidal silver in the frame of the present disclosure is a colloidal silver solution, i.e. a suspension of microscopically dispersed insoluble particles of silver in a liquid, typically in water, that does not settle or takes a long time to appreciably settle. The dispersed-phase particles have a diameter between approximately 1 and 1000 nanometers. Colloidal silver is commercially available for example under the trademark Collargol (available from Laboratorios Argenol).

The antibiotic of the nanosystem according to the second aspect of the present disclosure is preferably selected from, but is not limited to, penicillins (including aminopenicillins, antipseudomonal penicillins, beta-lactamase inhibitors, natural penicillins, and penicillinase resistant penicillins), cephalosporins, monobactams, beta lactamase inhibitors, carbapenems, aminoglucosides, quinolones, tetracyclines, glycopeptides, lincomycins, macrolides, ketolides, sulfonamides, aminoglycosides, oxazolidinones or from the group comprising colistin, sulfamethoxazole/trimethoprim, fosfomycin, nitrofurantoin, chloramphenicol, clindamycin, fusidic acid, linezolid, mupirocin, daptomycin, clindamycin and rifampicin. The definitions, examples and preferred antibiotics defined above with regard to the first aspect of the disclosure are applicable also, in all its scope and detail, to the second aspect of the disclosure, and are to be considered to be incorporated herein.

The resistant bacterial strain may be a gram negative or a gram positive strain. A gram negative strain is preferably selected from *Pseudomonas aeruginosa* (*Ps. aeruginosa*), *Escherichia coli* (*E. coli*), *Citrobacter freundii* (*C. freundii*), *Klebsiella oxitocca* (*K oxitocca*) and *Klebsiella pneumoniae* (*K pneumoniae*). A gram positive strain is preferably selected from *Staphylococcus aureus* (*S. aureus*) and *Staphylococcus epidermidis* (*S. epidermidis*).

The term "resistant to at least one antibiotic", means that the bacterial strain has a reduced sensitivity, or even absence of sensitivity, against the one antibiotic, in comparison with a wild type strain. Reduced sensitivity, in the frame of the present disclosure, refers to a MIC which is 15% above the MIC of the wild type strain, preferably to a MIC which is 25% above the MIC of the wild type strain, and most preferably to a MIC which is 50% above the MIC of the wild type strain.

The inventors have confirmed the usefulness of the compositions of the disclosure in the treatment of different bacterial strains. For example, the infection is caused by at least one strain of gram negative bacteria, which is resistant to at least one antibiotic. Preferably, the antibiotic used corresponds to the same antibiotic to which the bacterial strain is resistant.

For example, the composition according to the first aspect of the disclosure, wherein the carrier is an inert carrier, preferably kaolin, in combination with an antibiotic, preferably a penicillin, even more preferably Penicillin G, is for use in the treatment of an infection caused by a gram negative bacterial strain, preferably a strain selected from *E. Coli, C. freundii, K pneumoniae* or *Ps. aeruginosa*, even more preferably *E.coli* ATCC 8739, *E.coli* not BLEE, *E. coli* H24 BLEE+, *E. coli* C93 BLEE+, *E. coli* W207 BLEE+, *C. freundii* H44 BLEE+, *K. pneumoniae* ATCC 700603, *K. pneumoniae* (BLEE+), *Ps. aeruginosa* PAO1, *Ps. aeruginosa* OPRD, *Ps. aeruginosa* MEXR or *Ps. aeruginosa* VIM2, wherein BLEE+ means strain producing β-lactamase of extended spectrum.

For example, the composition according to the first aspect of the disclosure, wherein the carrier is an antibiotic, preferably a Penicillin, even more preferably Penicillin G, is for use in the treatment of an infection caused by a gram negative bacterial strain, preferably a strain selected from *E. Coli, C. freundii, K pneumoniae* or *Ps. aeruginosa*, even more preferably *E. coli* AC8 BLEE+, *E. coli* H24 BLEE+, *E. coli* C93 BLEE+, *E. coli* W207 BLEE+, *C. freundii* BLEE+, *K. pneumoniae* ATCC700603 BLEE+, *K. pneumo-* niae BLEE+, *Ps. aeruginosa* PAO1, *Ps. aeruginosa* OPRD, *Ps. aeruginosa* MEXR, *Ps. aeruginosa* DACB or *Ps. aeruginosa* VIM2, wherein BLEE+ means strain producing β-lactamase of extended spectrum.

For example, when the nanosystem of the disclosure comprises silver nanoparticles (either in suspension or in the form of colloidal silver) in combination with an antibiotic, the antibiotic preferably selected from Ampicillin, Piperacillin, Mezlocillin, Oxacillin, Penicillin, Penicillin G, Cefazolin, Cefuroxime, Cefpodoxime, Cefotaxime, Ceftazidime, Cefoxitin, Cefepime, Aztreonam, Amoxicilline/Clavulanic Acid, Ampicilline/Sulbactam, Piperacillin/tazobactam, Cefotaxime/Clavulanic Acid and Ceftazidime/Clavulanic Acid, Ertapenem, Meropenem, Imipenem, Amikacin, Gentamicin, Tobramycin, Levofloxacin, Ciprofloxacin, Moxifloxacin, Norfloxacin, Tetracycline, Tigecycline, Azithromycin, Erythromycin, Vancomycin, Teicoplanin, Colistin, Trimethoprim/Sulfamethoxazole, Fosfomycin, Nitrofurantoin, Chloramphenicol, Linezolid, Mupirocin, Daptomycin, Clindamycin, Rifampicin and Fusidic acid, is for use in the treatment of an infection, caused by a bacterial strain being resistant to at least one antibiotic, either a gram negative strain (selected from *Ps. aeruginosa, E. Coli, K pneumoniae* or *K. oxitocca*), or a gram positive strain (*S. aureus* or *S. epidermidis*); preferably, an infection caused by a gram negative strain, resistant to at least one antibiotic, even more preferably a gram negative bacterial strain selected from *Pseudomonas* VIM2 Mutant (metallo-β-lactamase producing), *Pseudomonas* OrpD Mutant (deficient in porin), *Presudomonas* MexR Mutant (efflux pump over-expression), *Pseudomonas* DacB Mutant (hiperproducing AMPC), *E. coli* BLEE+and *Klebsiella* BLEE+.

Further, the inventors have confirmed the usefulness of the compositions of the disclosure in the treatment of infections caused by non-resistant bacteria, making it possible to treat said infections with doses of the antibiotic lower than those that are generally prescribed or recommended; the use of lower doses of antibiotic when treating infections would reduce the onset of antibiotic resistance of bacteria, due to the lower exposure to the antibiotic, and thus the use of lower doses of antibiotic than those generally prescribed or recommended, in combination with silver nanoparticles, either supported on the antibiotic or in admixture with it, is also intended to be in the scope of the present disclosure.

Additionally, the present disclosure relates to a preparation process of the composition according to the first aspect of the disclosure as defined above, comprising the steps of:
  a) preparing a dissolution of a silver ion;
  b) adding said silver ion dissolution to a carrier in the form of particles;
  c) adding a reducing agent to the mixture obtained in b), to obtain metallic silver supported on said carrier; and
  d) in the case the carrier is an inert carrier, mixing with at least one antibiotic .

Particularly, when in the first aspect of the disclosure the carrier is an inert carrier, the preparation process comprises the steps of:
  a) preparing a dissolution of a silver ion;
  b) adding said silver ion dissolution to an inert carrier in the form of particles;
  c) adding a reducing agent to the mixture obtained in b), to obtain metallic silver supported on said inert carrier; and
  d) mixing the metallic silver supported inert carrier with at least one antibiotic to obtain the composition wherein the carrier is an inert carrier.

The compositions of the disclosure wherein the metallic silver nanoparticles are supported on an inert carrier may thus be obtained by the above method.

Particularly, when in the first aspect of the disclosure the carrier is an antibiotic, the preparation process comprises the steps of:
  a) preparing a dissolution of a silver ion;
  b) adding said silver ion dissolution to an antibiotic in the form of particles;
  c) adding a reducing agent to the mixture obtained in b), to obtain metallic silver supported on said antibiotic particles.

The compositions of the disclosure wherein the metallic silver nanoparticles are supported on an antibiotic may thus be obtained by the above method.

In the frame of the present disclosure, the silver ions may be obtained by dissolving any inorganic salt, e.g. a salt selected from the group consisting of silver chloride, silver sulfide, silver carbonate, or silver nitrate. Silver ions may be also obtained by using silver oxide. Preferably, the silver ions are obtained by using silver oxide or silver nitrate. Most preferred is silver oxide.

The reducing agent used in the present disclosure may be selected, but is not limited to, from the group consisting of hydroquinone, formol, hydrazine sulphate, ascorbic acid and reducing sugars. Preferable reducing agents are hydrazine sulfate and ascorbic acid.

The above mentioned processes comprise the essential steps to carry out the disclosure; in the following, a further detailed process is described, comprising further, not essential, intermediate steps, and is in no case intended to limit the scope of the disclosure. In step (a) a silver ion is dissolved, using the amount necessary to obtain the aimed concentration of silver in the final product. Once dissolved, silver oxide is precipitated by adding a suitable basifying agent, such as, for example, sodium hydroxide, in a suitable amount determined by the skilled person, until no further precipitation is observed. Said precipitate is redissolved by adding ammonia, in order to obtain a clear solution of an ammoniacal silver complex. Then in step b) this solution is added to the powdered inert carrier, in a reactor, at room temperature and under stirring, and kept stirring for several hours. The amount of inert carrier is calculated based on the amount of silver to be supported. Then in step a reducing agent is added, in order to reduce ionic silver (deposited on the inert carrier) to metallic silver. Said reducing agent may be a reducing compound, or a mixture of reducing compounds, according to the State of the Art. Finally, as much water as possible is removed from the obtained solid, e.g. by centrifugation or filtering. Subsequently, the product is dried at a temperature somewhat above room temperature in a suitable drying device.

In the following, the present disclosure will be described in even more detail based on examples; nevertheless, in no case the scope of the present disclosure is to be limited to the examples.

EXAMPLES

Example 1: Antibiograms of Penicillin G Alone and in Combination with Silver Nanoparticles Supported on Kaolin In Example 1 the antimicrobial activity against Gram negative bacteria of penicillin G alone and penicillin G in combination with silver nanoparticles supported on kaolin was tested, by means of antibiograms. Diverse strains of Gram negative bacterial species have been used for said testing. Both reference strains (ATCC) and strains with some resistance or mutation (e.g., beta-lactamase producers, vancomycin resistant) were selected. The strains used are listed below in Table 1:

TABLE 1

List and features of Gram-negative strains

| Strain | Identification/origin | Features |
|---|---|---|
| E. coli | ATCC 8739 | Reference strain |
| E. coli | Clinical isolate (Clinica Universidad de Navarra) | Not BLEE |
| E. coli H24 | Isolate from healthy patient | BLEE+ |
| E. coli C93 | Clinical isolate (Clinica Universidad de Navarra) | BLEE+ |
| E. coli W207 | Isolate from river water | BLEE+ |
| C. freundii | Isolate from healthy patient | BLEE+ |
| K. pneumoniae | ATCC 700603 | BLEE+ (SHV-18) |
| K. pneumoniae | Clinical isolate (Clinica Universidad de Navarra) | BLEE+ |
| Ps. aeruginosa | PAO1 | Wild type phenotype (not resistant) |
| Ps. aeruginosa | OPRD | OprD (porin) deficient mutant of PAO1 |
| Ps. aeruginosa | MEXR | Mutant of PAO1 (mexR) with MexAB-OprM overexpression (efflux pump) |
| Ps. aeruginosa | VIM2 | PAO1 with cloned VIM2 (metallo-β-lactamase production) |

BLEE+: strain producing β-lactamase of extended spectrum

From the stock cultures, which were maintained at −80±5° C., revitalization of the strains (TSB, TSA and blood agar cultures, incubation at 37° C., 24 h) and preparation of working cultures (maintenance at 5° C.±3° C.) was carried out.

The study of microbial activity of the products was performed by the agar diffusion method (antibiograms). Preliminary experiments were performed to adjust the concentration of each strain to obtain a homogeneous field, and select the appropriate culture medium (in this case, Mueller Hinton agar). Whenever possible, large Petri plates (135 mm diameter) were used, but when the halo was too large, several plates of 90 mm diameter were used to test all the products. The procedure was as follows:
  Preparation of fresh cultures of each of the strains on agar (37° C., 24 h).
  Transferring to BHI broth (37° C., 24 h) and adjusting the inoculum, and performing serial dilutions in Mueller Hinton broth. Addition of 1-2 ml of the corresponding dilution to sterile Petri plates (depending on size) and then pouring Mueller Hinton agar, tempered to 45° C. Allowing the agar to solidify at room temperature and then practicing wells in which the products to be tested will be placed.
  Preparing the test substances in the appropriate concentration (suspension of 1 mg/ml in sterile water and serial dilutions). Placing 50 μl of the chosen concentration in each well (a previous study was done to determine which concentration provided the most appropriate halos in each strain). As a positive control, Penicillin G (at the same concentration) was used.
  Incubation of the plates at 37±1° C. for 24 hours. Then the inhibition halos observed in each well were measured and gathered in Table 2 below.

The Table 2 below shows the inhibition halos observed for each of the strains (the product concentration used is indicated within brackets, as in the case of resistant strains a higher concentration had to be used).

TABLE 2

Inhibition halos (mm) of the test products for strains of Gram-negative bacteria

| STRAIN* (concentration μg/ml) | PG | PG + NanoAg (Kaolin) |
|---|---|---|
| E. coli ATCC 8739 (50) | 21 | 18 |
| E. coli not BLEE (50) | 21 | 12 |
| E. coli H24 BLEE+ (50) | <1 | 11 |
| E. coli C93 BLEE+ (50) | <1 | 10 |
| E. coli W207 BLEE + (50) | <1 | 10 |
| C. freundii H44 BLEE+ (50) | <1 | 9 |
| K. pneumoniae ATCC 700603 (200) | <1 | 13 |
| K. pneumoniae BLEE+ (200) | <1 | 12 |
| Ps. aeruginosa PAO1 (50) | <1 | 8 |
| Ps. aeruginosa OPRD (50) | <1 | 12 |
| Ps. aeruginosa MEXR (50) | <1 | 9 |
| Ps. aeruginosa VIM2 (50) | <1 | 9 |

*in bold letters: strains with some resistance
PG: penicillin G
PG + NanoAg (Kaolin) Penicillin G + Silver nanoparticles supported on Caolin Example 2: Antibiograms of Penicillin G Alone and Penicillin G with Silver Nanoparticles Supported on it In Example 2 the antimicrobial activity against Gram negative bacteria of penicillin G alone and penicillin G having silver nanoparticles supported on it was tested, by means of antibiograms. Various strains of Gram negative bacterial species were used. Both reference strains (ATCC) and strains having some resistance or mutation (e.g., beta-lactamase producers, vancomycin resistant) were selected. See Table 3 below:

TABLE 3

List and features of Gram-negative strains used in the example

| Strain | Identification/origin | Features |
|---|---|---|
| E. coli AC8 | Isolate from food (chicken) | BLEE+ |
| E. coli H24 | Isolate from healthy carrier | BLEE+ |
| E. coli C93 | Clinical isolate (Clinica Universidad de Navarra) | BLEE+ |
| E. coli W207 | Isolate from river water | BLEE+ |
| C. freundii | Isolate from healthy carrier | BLEE+ |
| K. pneumoniae | ATCC 700603 | BLEE+ (SHV-18) |
| K. pneumoniae | Clinical isolate (Clinica Universidad de Navarra) | BLEE+ |
| Ps. aeruginosa | PAO1 | Wild type phenotype (not resistant) |
| Ps. aeruginosa | OPRD | OprD (porin) defficient mutant of PAO1 |

TABLE 3-continued

List and features of Gram-negative strains used in the example

| Strain | Identification/origin | Features |
|---|---|---|
| Ps. aeruginosa | MEXR | Mutant of PAO1 (mexR) with MexAB-OprM overexpression (efflux pump) |
| Ps. aeruginosa | DACB | PAO1 mutant overproducing AmpC |
| Ps. aeruginosa | VIM2 | PAO1 with cloned VIM2 (metallo-β-lactamase production) |

BLEE+: strain producing β-lactamase of extended spectrum

From the stock cultures, which were maintained at −80±5° C., revitalization of the strains (TSB, TSA and blood agar cultures, incubation at 37° C., 24 h) and preparation of working cultures (maintenance at 5° C.±3° C.) was carried out.

The study of microbial activity of the products was performed by the agar diffusion method (antibiograms). Preliminary experiments were performed to adjust the concentration of each strain to obtain a homogeneous field, and the appropriate culture medium (in this case, Mueller Hinton agar) was selected. Whenever possible, large Petri plates (diameter of 135 mm) were used, but when the halo was too large, several plates of 90 mm diameter were used to test all the products. The procedure was as follows:

- Preparation of fresh cultures of each of the strains on agar (37° C., 24 h).
- Transferring to BHI broth (37° C., 24 h) and adjusting the inoculum, performing serial dilutions in Mueller Hinton broth. Addition of 1-2 ml of the corresponding dilution to sterile Petri plates (depending on size) and then pouring Mueller Hinton agar, tempered to 45° C. Allowing the agar to solidify at room temperature and then practicing wells in which the products will be placed to be tested.
- Preparing the test substances in the appropriate concentration (suspension of 1 mg/ml in sterile water and serial dilutions). Placing 50 μl of the chosen concentration in each well (a previous study was done to see which concentration provided the most appropriate halos in each strain). As a positive control Penicillin G (at the same concentration) was used.
- Incubation of the plates at 3±1° C. for 24 hours. Then the inhibition halos observed in each well were measured and gathered in Table 4 below.

Table 4 shows the inhibition halos observed for each of the strains (the product concentration used is indicated within brackets, as in the case of resistant strains a higher concentration had to be used).

TABLE 4

Inhibition halos (mm) of the test products for strains of Gram-negative bacteria

| STRAIN* (concentration μg/ml) | PG | 7A | 7B |
|---|---|---|---|
| E. coli AC8 BLEE+ (50) | <1 | 13 | 13 |
| E. coli H24 BLEE+ (50) | <1 | 14 | 14 |
| E. coli C93 BLEE+ (50) | <1 | 13 | 13 |
| E. coli W207 BLEE+ (50) | <1 | 13 | 12 |
| C. freundii H44 BLEE+ (50) | <1 | 10 | 10 |
| K. pneumoniae ATCC 700603 (200) | <1 | 16 | 16 |
| K. pneumoniae BLEE+ (200) | <1 | 14 | 14 |
| Ps. aeruginosa PAO1 (50) | <1 | 15 | 15 |
| Ps. aeruginosa OPRD (50) | <1 | 15 | 15 |
| Ps. aeruginosa MEXR (50) | <1 | 13 | 12 |
| Ps. aeruginosa DACB (50) | 9 | 14 | 14 |
| Ps. aeruginosa VIM2 (50) | <1 | 13 | 12 |

PG: penicillin G
7A: Silver nanoparticles supported on penicillin G (source of silver: silver oxide; reducing agent: hydrazine sulfate)
7B: Silver nanoparticles supported on penicillin G source of silver: silver oxide; reducing agent: ascorbic acid)

Example 3: Determination of MIC and MBC for Colargol (Colloidal Silver)

In Example 3 the values of MIC (Minimum Inhibitory Concentration) and MBC (Minimum Bactericidal Concentration) of Colargol (colloidal silver) for both Gram positive and Gram negative strains were determined, using the microdilution plate technique.

MIC: minimum concentration that inhibits microorganism growth (absence of turbidity)

MBC: minimum concentration that destroys 99.9% of the initial microbial population (requires counting the surviving population and comparing with the initial concentration of microorganisms)

Strains of both Gram positive and Gram negative microorganisms have been used, which present various types of resistance, as well as reference strains (ATCC), having non-resistant phenotypes. The species included in the testing are indicated in Table 5 below:

TABLE 5

List and features of the Gram-negative strains used in the study

| N° | Strain | Identification | Features |
|---|---|---|---|
| 1 | Ps. aeruginosa | PAO1 | Wild type phenotype (Non-resistant) |
| 2 | Ps. aeruginosa | PAOD1 | OprD (porin) defficient mutant of PAO1 |
| 3 | Ps. aeruginosa | PAOΔAmexZ:Gm | Mutant of PAO1 (mexR) with MexAB-OprM overexpression (Efflux pump) |
| 4 | Ps. aeruginosa | PAO1ΔDacB | PAO1 mutant overproducing AmpC |
| 5 | Ps. aeruginosa | AO1pUCP24/VIM2 | PAO1 with cloned VIM2 (metallo-β-lactamase production) |
| 6 | Ps. aeruginosa | ATCC 9027 | Reference strain (Non-resistant) |
| 7 | E. coli | BLEE+ | Clinical isolate (β-lactam - resistant) |

TABLE 5-continued

List and features of the Gram-negative strains used in the study

| N° | Strain | Identification | Features |
|----|--------|----------------|----------|
| 8  | E. coli | Not BLEE | Clinical isolate (Non-resistant) |
| 9  | E. coli | ATCC 8739 | Reference strain (Non-resistant) |
| 10 | K. pneumoniae | BLEE+ | Clinical isolate (β-lactam - resistant) |
| 11 | K. oxytocca | NCTC 8167 | Reference strain (Non-resistant) |
| 12 | S. aureus MRSA | ATCC 700698 | Methicillin resistant and sensitive to vancomycin |
| 13 | S. aureus MRSA | ATCC 700789 | Methicillin resistant and intermediate resistance to vancomycin |
| 14 | S. aureus | ATCC 6538P | Reference strain (Non-resistant) |

In the following some further details regarding the strains are provided:

Pseudomonas aeruginosa resistant to β-lactams:

5 strains of Ps. aeruginosa were used, including a reference strain having a wild type phenotype (non-resistant) and 4 mutants derived therefrom, which are resistant to β-lactam antibiotics by different mechanisms (efflux pump overexpression, deficiency in porins, production of metallo β-lactamases, etc).

An antibiotic sensitivity study was carried out by Vitek method, obtaining the following profiles:

PAO1: sensitive to most antibiotics tested

PAOD1: carbapenem resistant (impermeability)

PAOΔmexZ:Gm: acquired penicillinase resistance+carbapenems resistance

PAO1ΔDacB: resistance to high level β-lactams

PAO1pUCP24/VIM2: carbapenemase producer (metallo-UOX(A)

E. coli and Klebsiella pneumoniae resistant to cephalosporins:

2 strains of β-lactamases producing Enterobacteriaceae of extended spectrum (BLEE) were used.

Methicillin resistant Staphylococcus aureus:

2 reference S. aureus strains (ATCC) were used, resistant to methicillin. One also has intermediate resistance to vancomycin.

The revitalization of the strains (cultures in TSB and TSA, incubation at 37° C., 24 h) was carried out, their features (biochemical and antibiotic sensitivity testing by the automated method Vitek) were checked, and the working cultures (maintenance±3° C. to 5° C.) and stock cultures (−80±5° C. maintenance) were prepared.

The procedure to determine MIC and MBC of Colargol (colloidal silver) was as follows:

Preparation of fresh cultures of each of the strains on TSA agar (37° C., 24 h).

Transfer to BHI (brain heart infusion) broth (37° C., 24 h) and adjusting the inoculum in a spectrophotometer at 600 nm, to obtain a concentration of about $1.0 \times 10^8$ CFU/ml. From the adjusted inoculum, a 1/100 dilution was prepared and the initial concentration of each microorganism was determined by plate counting (serial dilutions and duplicate seeding in TSA agar).

Preparation of 96-well sterile Microtiter plates with each of the strains (triplicate assays for each of the conditions tested; when differences of more than one well were obtained from the three replicates, the assay was repeated). To each well (except for the negative control) 0.1 ml of the prepared inoculum (initial concentration in each well around $1.0 \times 10^5$ CFU/ml) was added:

Colargol 70%: twofold dilutions in Mueller Hinton broth (490 ppm to 0.12 ppm or mg/ml)+microorganism Positive control: Mueller Hinton broth+microorganism Negative control: only Mueller Hinton broth Incubation of the plates (37° C., 24 h) and determining the MIC by observation of turbidity (lowest concentration at which no growth is observed).

In order to determine MBC, seeding was performed on TSA agar from each of the wells (5-6 dilutions). After incubating at 37° C. for 24 h and counting the UFC (expressed in CFU/ml), the concentration that destroys 99.9% of the population (compared to the initial count for each microorganism) was determined.

Table 6 below shows the average value obtained in the three replicates per strain and condition.

TABLE 6

List and characteristics of Gram-negative strains used in the study

| Strain | Initial concentration (CFU/ml) | MIC (µg/ml) | MBC µg/ml |
|--------|-------------------------------|-------------|-----------|
| Ps. aeruginosa PAO1 (wild) | $8.3 \times 10^4$ | 3.75 | 15 |
| Ps. aeruginosa PAOD1 (porine mutant) | $7.9 \times 10^4$ | 3.75 | 15 |
| Ps. aeruginosa PAO1 (pumb mutant) | $8.0 \times 10^4$ | 3.75 | 15 |
| Ps. aeruginosa PAO1 (AmpC) | $8.6 \times 10^4$ | 3.75 | 15 |
| Ps. aeruginosa PAO1 (metallo-β-lactam) | $1.1 \times 10^5$ | 3.75 | 15 |
| Ps. aeruginosa ATCC 9027 (reference) | $9.7 \times 10^4$ | 31 | 62 |
| E. coli BLEE+ | $8.3 \times 10^4$ | 3.75 | 3.75 |
| E. coli not BLEE | $1.1 \times 10^5$ | 3.75 | 3.75 |
| E. coli ATCC 8739 (reference) | $5.7 \times 10^4$ | 3.75 | 3.75 |
| K. pneumoniae BLEE+ | $8.1 \times 10^4$ | 62 | 123 |
| K. oxytocca NCTC 8167 (reference) | $1.1 \times 10^5$ | 3.75 | 15 |
| S. aureus ATCC 700698 | $7.9 \times 10^4$ | 62 | 490 |
| S. aureus ATCC 700789 | $7.7 \times 10^4$ | 62 | >490 |
| S. aureus ATCC 6538P (reference) | $5.4 \times 10^4$ | 62 | 245 |

Example 4: Silver-Antibiotics Interaction Study

The effect of subinhibitory concentrations of colloidal silver (namely, ½ and 1/10 dilution of the MIC obtained in Example 3) in the presence of different types of antibiotics was tested.

For this, an automated equipment MicroScan AutoScan 4 (Siemens) was used, using Gram negative (Becman Coulter NM37) and Gram positive (Becman Coulter PM28) cards. The tested antibiotics are shown in Table 7.

The procedure was as follows:

Triplicate tests with inocula prepared on different days were performed:

Preparation of fresh cultures of each of the strains on TSA agar (37° C., 24 h).

Preparation of 3 prompt system-D bottles (Beckman Coulter) for each strain:
Control without silver
Silver at ½ MIC
Silver at 1/10 MIC
Inoculation of the bottles with sterile lancets to obtain a concentration equivalent to 0.5 McFarland. Each of these broths served as inoculum for the cards with antibiotics (for each strain, thus 3 cards were prepared).
Incubating the plates with antibiotics (in presence and absence of silver) at 37° C. for 24 h.
Reading the cards by use of LabPro software, and interpretation of the obtained values of MIC (determine if the silver reduces the initial MCI of each antibiotic).

TABLE 7

List of antibiotics used in MicroScan equipment

| Gram negative | Gram positive |
|---|---|
| Penicillins | |
| Ampicillin | Oxacillin |
| Piperacillin | Penicillin |
| Mezlocillin | Ampicillin |
| Cephalosporins | |
| Cefazolin | Cefepime |
| Cefuroxime | Cefuroxime |
| Cefpodoxime | |
| Cefotaxime | |
| Ceftazidime | |
| Cefoxitin | |
| Cefepime | |
| Monobactams | |
| Aztreonam | |
| β-lactamase inhibitors | |
| Amoxicilline/Clavulanic Acid | Amoxicilline/Clavulanic Acid |
| Ampicilline/Sulbactam | |
| Piperacillin/tazobactam | |
| Cefotaxime/Clavulanic Acid | |
| Ceftazidime/Clavulanic Acid | |
| Carbapenems | |
| Ertapenem | Ertapenem |
| Meropenem | Meropenem |
| Imipenem | Imipenem |
| Aminoglycosides | |
| Amikacin | Gentamicin |
| Gentamicin | Tobramycin |
| Tobramycin | |
| Quinolones | |
| Levofloxacin | Levofloxacin |
| Ciprofloxacin | Ciprofloxacin |
| Moxifloxacin | Moxifloxacin |
| Norfloxacin | |
| Tetracyclines | |
| Tetracyclines | Tetracyclines |
| Tigecycline | Erythromycin |
| Azithromycin | |
| Glycopeptides | |
| Vancomycin | |
| Teicoplanin | |
| Others | |
| Colistin | Trimethoprim/Sulfamethoxazole |
| Trimethoprim/Sulfamethoxazole | Fosfomycin |
| Fosfomycin | Clindamycin |
| Nitrofurantoin | Nitrofurantoin |
| Chloramphenicol | Fusidic acid |
| Linezolid | |

TABLE 7-continued

List of antibiotics used in MicroScan equipment

| Gram negative | Gram positive |
|---|---|
| | Mupirocin |
| | Daptomycin |
| | Clindamycin |
| | Rifampicin |

Effect Against Gram Negative Bacteria

In general it is observed that in the case of the reference ATCC strains, the effect of silver is moderate, only some MCI improving in 1 or 2 dilutions. However, it is observed that silver has a positive effect on the strains having a resistant phenotype, achieving a change from a resistant profile (or intermediate) to a sensitive profile against several antibiotics. The effect is observed with the highest concentration of silver (dilution of ½ MIC), although in some cases it is also observed in the presence of 1/10 MIC concentration.

The results obtained are further detailed in the following:
*Pseudomonas* VIM2 Mutant (metallo-β-lactamase producing):
sensitivity to penicillins (Piperacillin and Mezlocillin), cephalosporins (Cefepime), β-lactamase inhibitors (Amp/sulbac and Piperacillin/tazobactam), Carbapenems (meropenem and imipenem) and Fosfomicine.

*Pseudomonas* OrpD Mutant (deficient in porin):
in this case, the 1/10 MIC silver concentration achieved sensitivity to Penicillines (Mezlocillin and Piperacillin), and β-lactamase inhibitors (Piperacillin/tazobactam). On the other hand, in the presence of ½ CIM concentration of silver, sensitivity against Cephalosporins (Ceftazidime, Cefepime), monobactams (aztreonam) and Fosfomycin was achieved.

*Pseudomonas* MexR Mutant (efflux pump over-expression):
in the presence of silver at a concentration of ½ CMI, sensitivity to fosfomycin is observed, and an improvement in the MIC of cefotaxime, amp/sulbac and colistin is observed.

*Pseudomonas* DacB Mutant (hiperproducing AMPC):
silver has a positive effect, achieving a change to sensitive to fosfomycin and aztreonam, and a moderate effect improving the MIC values for piperacillin, cefepime, Piperacillin/tazobactam and colistin.

*E. coli* BLEE +:
the strain becomes sensitive to penicillins and cephalosporins, beta-lactamase inhibitors (Amp/sulbac), aminoglycosides (gentamicin and tobramycin), quinolones, tetracycline and trim/sulfa.

*Klebsiella* BLEE +:
the strain becomes sensitive to penicillins, most of cephalosporins, to aztreonam, Amp/sulbac, quinolones, tetracycline and trim/sulfa.

Thus, the silver improves the action of the antibiotics with which it is combined, on bacteria which present antibiotic resistance.

Effect Against Gram Positive Bacteria

An improved sensitivity towards quinolones (including vancomycin) is observed. In the case e.g. of strain SA700698, it is observed that silver also favours the action of carbapenems.

Example 5: Evaluation of the Presence of an Additive Effect or Synergy for Collargol in Combination with Antibiotics using Epsilometry E-test An epsilometry E-test was carried out to determine the presence of an additive or sinergical effect of Collargol in presence of antibiotics. Strains of *Staphylococcus aureus* and *Staphylococcus epidermidis* of clinical origin were used, exhibiting elevated MIC to vancomycin (≥1.5 μg/ml). (Table 1).

TABLE 8

List and features of Gram-negative strains used in the study

| N° | Strain | Identification | Features |
|---|---|---|---|
| 1 | S. aureus | Sa-1 | Vancomycin ≥ 1.5 |
| 3 | S. aureus | Sa-3 | Vancomycin ≥ 1.5 |

TABLE 8-continued

List and features of Gram-negative strains used in the study

| N° | Strain | Identification | Features |
|---|---|---|---|
| 8 | S. aureus | Sa-9 | Vancomycin ≥ 1.5 |
| 9 | S. aureus | Sa-10 | Vancomycin ≥ 1.5 |
| 10 | S. aureus | Sa-11 | Vancomycin ≥ 1.5 |
| 11 | S. aureus | Sa-12 | Vancomycin ≥ 1.5 |
| 12 | S. aureus | Sa-13 | Vancomycin ≥ 1.5 |
| 13 | S. aureus | Sa-14 | Vancomycin ≥ 1.5 |
| 14 | S. epidermidis | Se-1 | Vancomycin ≥ 1.5 |
| 15 | S.aureus ATCC 700698 | Sa-SARM | Vancomycin ≥ 1.5 |

In order to evaluate the synergy of collargol-antibiotics an epsilometry E-test was carried out. Said test is based on the agar diffusion method and relates to using a strip with a predefined steady gradient of 15 concentrations of the antibiotic being tested. After strain growth, an elliptical inhibition halo, being the MIC the antibiotic concentration corresponding to the cutting point.

It was performed for the antibiotics vancomycin, linezolid and tedizolid, in absence and presence of silver (½ and ⅒ MIC). The procedure was as follows:

Preparation of fresh cultures of each of the strains on blood agar (37° C., 24 h).

Preparation of Mueller-Hinton (MET) agar plates, without silver and supplemented with ½ and ⅒ MIC (MH-½; MH-⅒), determined for each strain in previous trials (3 plates for each type per strain).

Prepare for each of the strains a 0.5 McFarland suspension (Promp system-D inoculation bottles) and extend the inoculum on the surface of the MH agar plates.

Place the strips of E-test and incubate at 37° C., 24 h.

Determine the MIC for each antibiotic in presence and absence of silver, according to the cutting point in the obtained elliptical halo.

Table 9 below shows the MIC value (cutting point) obtained in the three MH plates per strain and antibiotic.

TABLE 9

MIC values obtained in the E-test assay in the absence and presence of silver (½ and ⅒ MIC of colargol)

| | Linezolid (μg/ml) | | | Vancomycin (μg/ml) | | | Tedizolid (μg/ml) | | |
|---|---|---|---|---|---|---|---|---|---|
| Strain | MH (without silver) | MH-⅒ MIC | MH-½ MIC | MH (without silver) | MH-⅒ MIC | MH-½ MIC | MH (without silver) | MH-⅒ MIC | MH-½ MIC |
| 1 | NP | NP | NP | 0.5 | 0.5 | 0.38 | 0.19 | 0.25 | 0.19 |
| 3 | 1.5 | 1.5 | 1.0 | 0.75 | 0.75 | 0.38 | 0.19 | 0.19 | 0.125 |
| 8 | NP | NP | NP | 1.0 | 1.0 | 0.75 | 0.25 | 0.19 | 0.19 |
| 9 | 0.75 | 1.0 | 0.75 | 1.0 | 1.0 | 0.38 | 0.5 | 0.38 | 0.38 |
| 10 | 1.5 | 1.5 | 1.5 | 0.5 | 0.38 | 0.25 | 0.38 | 0.25 | 0.25 |
| 11 | 1.0 | 0.5 | 0.5 | 1.0 | 1.0 | 0.5 | 0.25 | 0.25 | 0.25 |
| 12 | 0.5 | 0.38 | 0.5 | 0.5 | 0.5 | 0.38 | NP | NP | NP |
| 13 | NP | NP | NP | 0.38 | 0.38 | 0.25 | NP | NP | NP |
| 14 | 0.75 | 0.75 | 0.5 | 0.75 | 0.5 | 0.38 | 0.38 | 0.38 | 0.25 |
| 15 | 0.5 | 0.5 | 0.38 | 1.5 | 1.0 | 1.0 | NP | NP | NP |

NP: Not performed

The figures in bold letters show the strains for which a reduced MIC in the presence of silver was observed. In most strains a lowering of the MIC was observed in the presence of silver (½ MIC).

Those strains that showed a marked decrease of MIC against vancomycin and somewhat moderate compared to other antibiotics were selected. Thus, strains 3, 9, 10, 11 and 14 (marked in bold italics) were selected for the Checkerboard synergy study.

To determine the existence of synergistic activity between collargol and vancomycin, a checkerboard test using plates having a "U"-shaped bottom (TPP) of 96 wells was used. Double subinhibitory serial dilutions of the two antimicrobials were prepared, so that the concentration of collargol decreased vertically (up-down) and the concentration of vancomycin decreased horizontally (left-right). See Table 10 below.

TABLE 10

Collargol and vancomycin concentrations per well

| | Concentration | 1 | 2 | 3 | 4 | 5 | 6 | 7 | 8 | 9 | 10 | 11 | 12 |
|---|---|---|---|---|---|---|---|---|---|---|---|---|---|
| A | Vancomycin (μg/ml) | 8 | 4 | 2 | 1 | 0.5 | 0.25 | 0.125 | 0.06 | 0.03 | 0.016 | C+ | C− |
| | Collargol (μg silver/ml) | 124 | 124 | 124 | 124 | 124 | 124 | 124 | 124 | 124 | 124 | C+ | C− |

TABLE 10-continued

Collargol and vancomycin concentrations per well

| | Concentration | 1 | 2 | 3 | 4 | 5 | 6 | 7 | 8 | 9 | 10 | 11 | 12 |
|---|---|---|---|---|---|---|---|---|---|---|---|---|---|
| B | Vancomycin (µg/ml) | 8 | 4 | 2 | 1 | 0.5 | 0.25 | 0.125 | 0.06 | 0.03 | 0.016 | C+ | C− |
| | Collargol (µg silver/ml) | 62 | 62 | 62 | 62 | 62 | 62 | 62 | 62 | 62 | 62 | C+ | C− |
| C | Vancomycin (µg/ml) | 8 | 4 | 2 | 1 | 0.5 | 0.25 | 0.125 | 0.06 | 0.03 | 0.016 | C+ | C− |
| | Collargol (µg silver/ml) | 31 | 31 | 31 | 31 | 31 | 31 | 31 | 31 | 31 | 31 | C+ | C− |
| D | Vancomycin (µg/ml) | 8 | 4 | 2 | 1 | 0.5 | 0.25 | 0.125 | 0.06 | 0.03 | 0.016 | C+ | C− |
| | Collargol (µg silver/ml) | 15.5 | 15.5 | 15.5 | 15.5 | 15.5 | 15.5 | 15.5 | 15.5 | 15.5 | 15.5 | C+ | C− |
| E | Vancomycin (µg/ml) | 8 | 4 | 2 | 1 | 0.5 | 0.25 | 0.125 | 0.06 | 0.03 | 0.016 | C+ | C− |
| | Collargol (µg silver/ml) | 7.8 | 7.8 | 7.8 | 7.8 | 7.8 | 7.8 | 7.8 | 7.8 | 7.8 | 7.8 | C+ | C− |
| F | Vancomycin (µg/ml) | 8 | 4 | 2 | 1 | 0.5 | 0.25 | 0.125 | 0.06 | 0.03 | 0.016 | C+ | C− |
| | Collargol (µg silver/ml) | 3.9 | 3.9 | 3.9 | 3.9 | 3.9 | 3.9 | 3.9 | 3.9 | 3.9 | 3.9 | C+ | C− |
| G | Vancomycin (µg/ml) | 490 | 245 | 123 | 61.5 | 31 | 15 | 7.7 | 3.8 | 1.9 | 0.95 | C+ | C− |
| | Collargol (µg silver/ml) | 0 | 0 | 0 | 0 | 0 | 0 | 0 | 0 | 0 | 0 | C+ | C− |
| H | Vancomycin (µg/ml) | 0 | 0 | 0 | 0 | 0 | 0 | 0 | 0 | 0 | 0 | C+ | C− |
| | Collargol (µg silver/ml) | 8 | 4 | 2 | 1 | 0.5 | 0.25 | 0.125 | 0.06 | 0.03 | 0.016 | C+ | C− |

To quantify the synergistic activity of the two combined compounds, the Index fractional inhibitory concentration (IFIC) parameter was used. This index relates MIC of the antimicrobial 1 with the antimicrobial 2 alone and in combination, according to the following formula:

$$IFIC = \frac{MIC \text{ (antimicrobial 1 in the combination)}}{MIC \text{ (antimicrobial 1)}} + \frac{MIC \text{ (antimicrobial 2 in the combination)}}{MIC \text{ (antimicrobial 2)}}$$

It is considered that there is synergistic effect if the IFIC value is <0.5. Other possible results are:
0.5<IFIC<1: additive effect
IFIC=1: no effect
IFIC>1: antagonism The procedure was as follows:
Preparation of fresh cultures of each of the strains on blood agar (37° C., 24 h). Prepare the inoculum, suspending colonies in MH broth, until an OD600nm of 0.085 (1/50 dilution of the suspension) is obtained.
Prepare solutions of collargol and vancomycin, considering the MIC obtained for each evaluated strain.
Prepare the wells as follows:
  Rows AF: Prepare double dilutions of collargol in MH, starting from the CMI (up to and including column 10).
  Columns 1 to 10: add the prepared double dilutions of vancomycin, starting from the CMI (up to and including row F).
  Controls: Row G collargol only (MIC control); Row H vancomycin only (MIC control); column 11 positive growth control (MH+inoculum); column 12 negativ control (MH);
Add the prepared inoculum to each well (except negative control column) and incubate the plates at 37° C. during 20-24 h.
Determine for each product, alone or combined, the MIC (lowest concentration at which no growth is observed) and calculate the IFIC for each row (last well wherein no growth is observed). The well wherein the minimum value of IFIC is obtained is chosen.

In Table 10 above, the cells comprising bold letters represent wells in which growth was observed.

The results obtained for each strain are shown in Table 11 below. In most of the cells an additive effect was observed, and some are in the limit of synergy (IIFIC=0.5)

TABLE 11

IFIC values obtained in the Checkerboard test

| Strain | Vancomicyn MIC (µg/ml) | Collargol CMI (µg/ml) | IFIC Calculations* | Value | Result |
|---|---|---|---|---|---|
| 3 | 1 | 61.5 | 0.5/1 + 30.5/61.5 | 0.99 | Additive effect |
| 9 | 1 | 61.5 | 0.5/1 + 3.8/61.5 | 0.56 | Additive effect (on the synergy limit) |
| 10 | 1 | 61.5 | 0.5/1 + 1.9/61.5 | 0.53 | Additive effect (on the synergy limit) |
| 11 | 1 | 31.0 | 0.5/1 + 15.5/31 | 1.0 | No effect |
| 14 | 1 | 61.5 | 0.5/1 + 1.9/61.5 | 0.53 | Additive effect (on the synergy limit) |

Example 6: Structural Characterization of Kaolin Supported with Silver Nanoparticles Regarding the characterization of silver supported on kaolin, an analysis of the particle size thereof by X-ray absorption has been performed, and images by scanning electron microscopy field emission (FESEM) have been obtained, in order to know the morphology of kaolin, as well as the way in which silver is deposited thereon FIG. 1 comprises images wherein spheroidal silver nanoparticles on the laminar structure of kaolin microparticles may be observed.

By EDX analysis, silver has been identified in said nanoparticles, having a size around 30 nm.

Figure 1D:
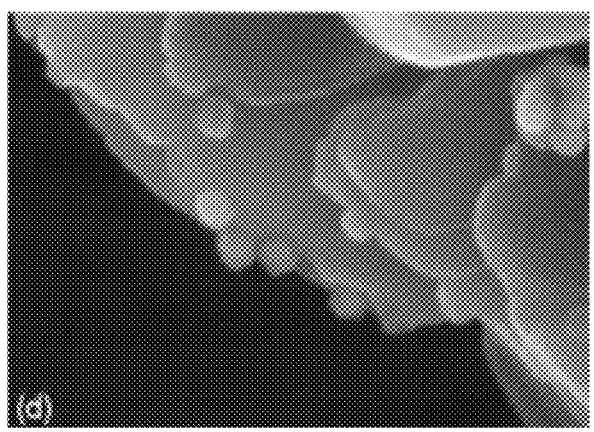

FIG. 1 represents the FESEM image of kaolin:

FIG. 1(a) shows Kaolin microparticles with deposited silver nanoparticles thereon (x8870).

FIG. 1(b) shows at x20380 the area highlighted in FIG. 1(a).

FIG. 1(c.1) shows at x66000 the area (c) highlighted in FIG. 1(b). Silver nanoparticles can be clearly appreciated on the surface of the laminar structure of Kaolin.

Silver nanoparticles (white color) can be further appreciated in FIG. 1(c.2) when observed under backscattered electrons, as opposed to areas having no Silver nanoparticles.

FIG. 1(d) shows at x66000 the area (d) highlighted in FIG. 1(b). Silver nanoparticles can be clearly appreciated on the edges of the laminar structure of Kaolin.

The presence of silver nanoparticles for the white areas in FIG. 1(c.2), was confirmed by EDX spectra.

The invention claimed is:

1. A composition, comprising metallic silver nanoparticles supported on a carrier, the carrier being in the form of particles, wherein the carrier is an antibiotic.

2. The composition according to claim 1, the particles having a mean diameter between 0.1 and 200 micrometers.

3. The composition according to claim 1, wherein the antibiotic is selected from penicillins, cephalosporins, monobactams, beta lactamase inhibitors, carbapenems, aminoglucosides, quinolones, tetracyclines, glicopeptides, colistin, sulfamethoxazole/trimethoprim, fosfomycin, nitrofurantoin, chloramphenicol, clindamycin, fusidic acid, linezolid, mupirocin, daptomycin, clindamycin and rifampicin.

4. The composition according to claim 1, wherein the weight ratio of silver with respect to the total amount of antibiotics is between 10:100 and 0.1:100.

5. The composition according to claim 1, wherein the mean particle size of the metallic silver nanoparticles is comprised between 1 and 100 nanometers.

6. A nanosystem comprising a composition according to claim 1 or a mixture of silver nanoparticles and at least one antibiotic, for use in the treatment of an infection caused by at least one strain of bacteria resistant to at least one antibiotic.

7. The nanosystem according to claim 6, wherein the infection is caused by at least one strain of gram negative bacteria, resistant to at least one antibiotic.

8. The nanosystem according to claim 6, which comprises a mixture of silver nanoparticles and an antibiotic, wherein the antibiotic is selected from penicillins, cephalosporins, monobactams, beta lactamase inhibitors, carbapenems, aminoglucosides, quinolones, tetracyclines, glicopeptides, colistin, sulfamethoxazole/trimethoprim, fosfomycin, nitrofurantoin, chloramphenicol, clindamycin, fusidic acid, linezolid, mupirocin, daptomycin, clindamycin and rifampicin.

9. The nanosystem according to claim 8, comprising colloidal silver nanoparticles and at least one antibiotic, for use in the treatment of an infection caused by at least one strain of bacteria resistant to at least one antibiotic.

10. The nanosystem according to claim 8, wherein the silver nanoparticles are used in a weight ratio with respect to the total amount of antibiotics between 1:100 and 0.1:100.

11. A preparation process of a composition according to claim 1, the process including the following steps:
    a) preparing a dissolution of a silver ion;
    b) adding said silver ion dissolution to a carrier in the form of particles, wherein the carrier is an antibiotic; and
    c) adding a reducing agent to the mixture obtained in b), to obtain metallic silver supported on said carrier.

12. A pharmaceutical composition which comprises at least one pharmaceutically acceptable excipient and a composition according to claim 1, for use as a medicament.

13. A pharmaceutical composition which comprises at least one pharmaceutically acceptable excipient and a composition according to claim 1, for use in the treatment of an infection.

14. A pharmaceutical composition which comprises at least one pharmaceutically acceptable excipient and a composition according to claim 1, for oral use in the treatment of an infection.

15. The composition according to claim 1, wherein the mean particle size of the metallic silver nanoparticles is comprised between 10 and 90 nanometers.

16. The composition according to claim 1, wherein the mean particle size of the metallic silver nanoparticles is comprised between 10 and 70 nanometers.

17. The composition according to claim 1, wherein the mean particle size of the metallic silver nanoparticles is comprised between 10 and 50 nanometers.

18. The composition according to claim 1, wherein the mean particle size of the metallic silver nanoparticles is comprised between 20 and 30 nanometers.

* * * * *